United States Patent

Dilnik

[11] Patent Number: 6,013,062
[45] Date of Patent: *Jan. 11, 2000

[54] FRANGIBLE SECUREMENT MEANS FOR INWARDLY DISPOSED SECUREMENT PANELS

[75] Inventor: Rebecca Lyn Dilnik, Neenah, Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/838,766

[22] Filed: Apr. 10, 1997

Related U.S. Application Data

[63] Continuation of application No. 08/512,947, Aug. 9, 1995, abandoned.

[51] Int. Cl.[7] ............................. A61F 13/15; A61F 13/20
[52] U.S. Cl. ..................... 604/385.1; 604/386; 604/387
[58] Field of Search ............................ 604/385.1, 387, 604/386, 389–371

[56] References Cited

U.S. PATENT DOCUMENTS

| | | | |
|---|---|---|---|
| 4,589,876 | 5/1986 | Ven Tilburg | 604/385.1 |
| 4,630,320 | 12/1986 | Van Gompel | 2/406 |
| 4,883,481 | 11/1989 | Blanchard | 604/385.1 |
| 5,133,705 | 7/1992 | Nakanishi et al. | 604/387 |
| 5,201,727 | 4/1993 | Nakanishi et al. | 604/386 |
| 5,221,275 | 6/1993 | Ven Item | 604/386 |
| 5,344,416 | 9/1994 | Niihara | 604/385.1 |
| 5,354,400 | 10/1994 | Lavash et al. | 156/227 |
| 5,387,210 | 2/1995 | Murakani | 604/387 |
| 5,389,094 | 2/1995 | Lavash et al. | 604/385.2 |
| 5,429,633 | 7/1995 | Davis et al. | 604/385.1 |
| 5,472,437 | 12/1995 | Akiyama et al. | 604/386 |
| 5,578,026 | 11/1996 | Lavash et al. | 604/387 |
| 5,591,147 | 1/1997 | Couture-Dorschner et al. | 604/369 |
| 5,643,245 | 7/1997 | Osborn et al. | 604/387 |

FOREIGN PATENT DOCUMENTS

| | | |
|---|---|---|
| 0511905A1 | 11/1992 | European Pat. Off. . |
| 0590675A1 | 4/1994 | European Pat. Off. . |
| 0595047A1 | 5/1994 | European Pat. Off. . |
| 2244653 | 12/1991 | United Kingdom . |
| WO92/07537 | 5/1992 | WIPO . |
| WO94/12135 | 6/1994 | WIPO . |
| WO94/13236 | 6/1994 | WIPO . |
| WO94/13237 | 6/1994 | WIPO . |
| WO94/27540 | 12/1994 | WIPO . |
| WO95/08311 | 3/1995 | WIPO . |

*Primary Examiner*—Mark O. Polutta
*Attorney, Agent, or Firm*—Mark L. Davis; Brian R. Tumm; Jerry F. Janssen

[57] ABSTRACT

An absorbent article, such as a sanitary napkin, is provided having an absorbent between a cover and a baffle. The absorbent article also includes an inwardly directed attachment panel adapted to be folded around at least a portion of the crotch of the undergarment. To facilitate ease of placing the sanitary napkin in an undergarment prior to use, the panel is held in an outward direction, relative to the longitudinal side of the absorbent, by a frangible securement bond. The frangible fastener is affixed to one surface of the panel and has a bond strength of less than about 500 grams. When the wearer is ready to secure the article in the undergarment, the bond is easily broken by the wearer and the panel is appropriately positioned.

19 Claims, 2 Drawing Sheets

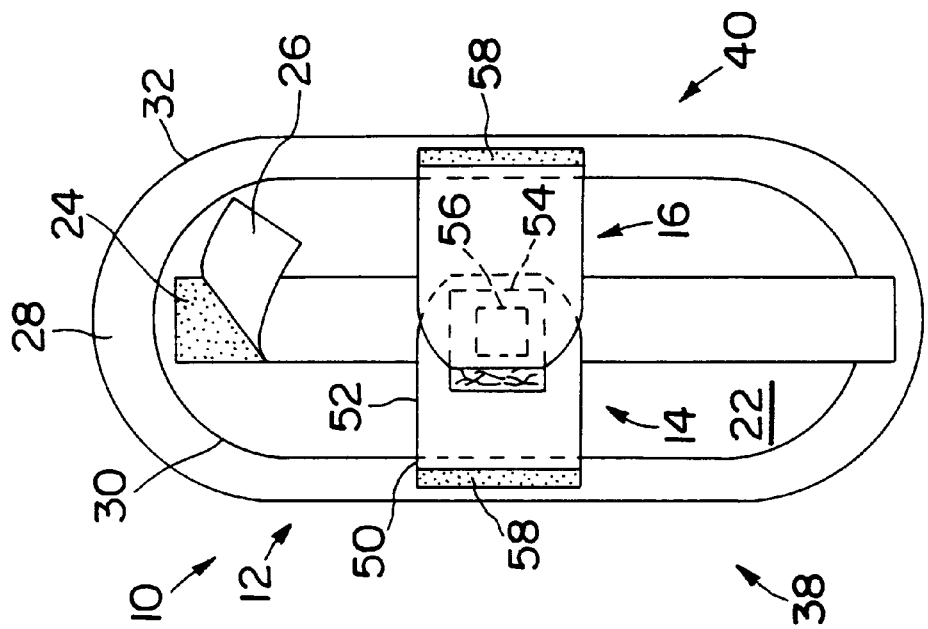
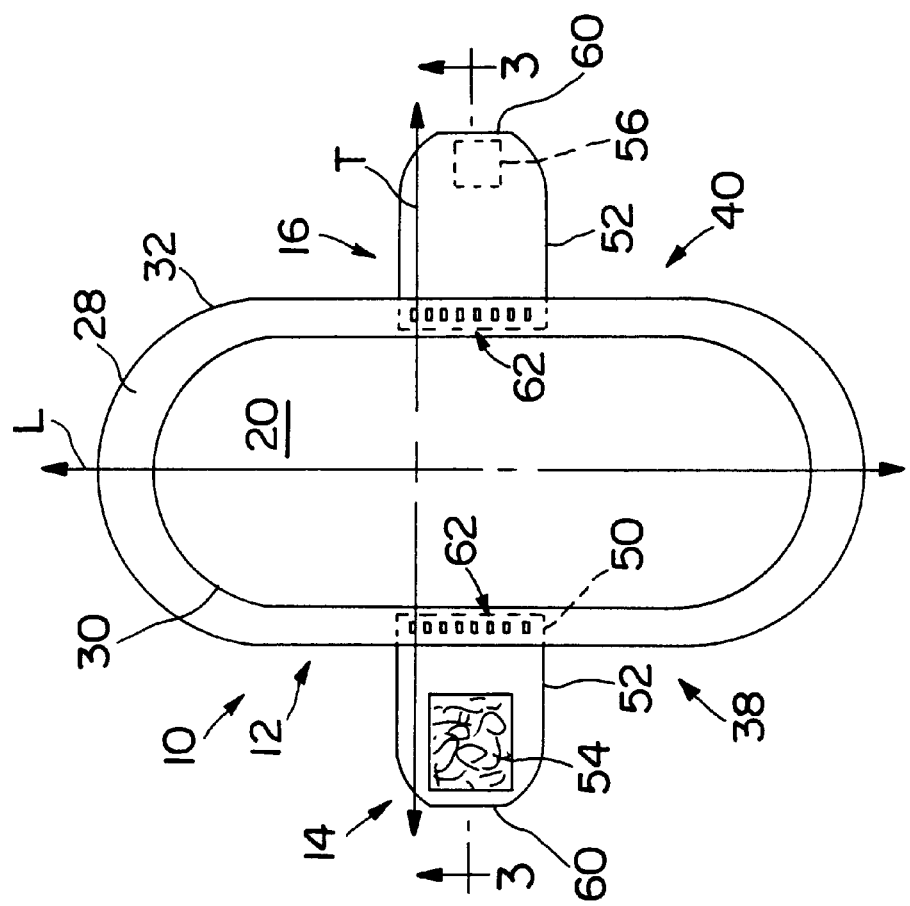

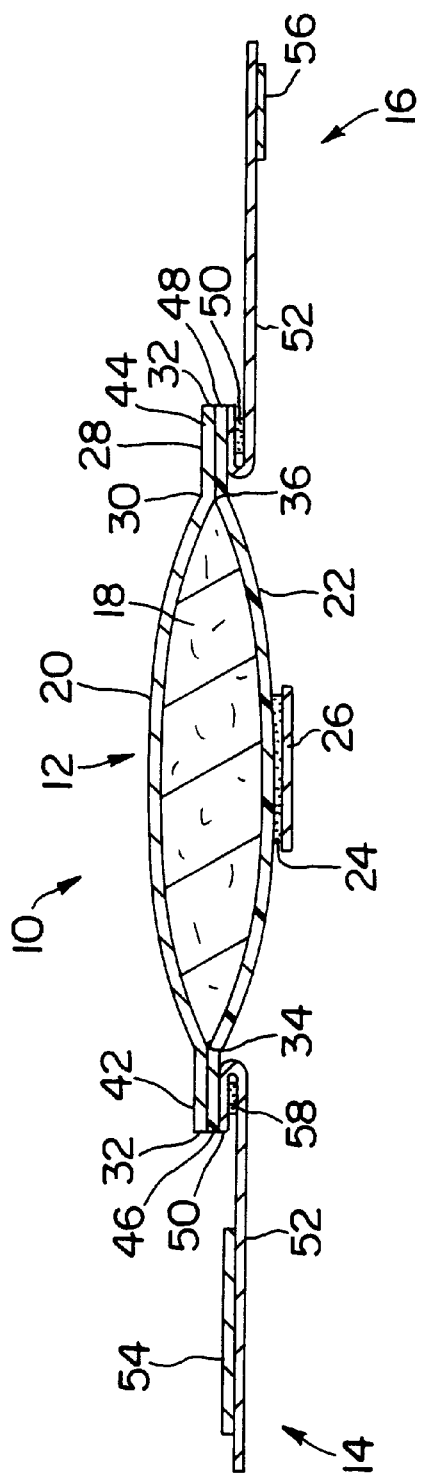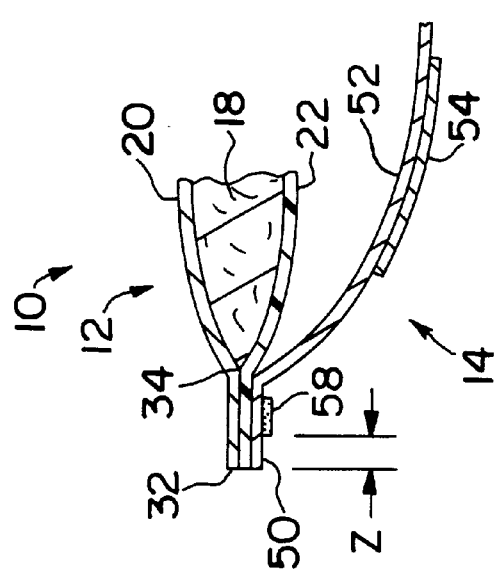

1

FRANGIBLE SECUREMENT MEANS FOR INWARDLY DISPOSED SECUREMENT PANELS

This application is a continuation of application Ser. No. 08/512,947 entitled "FRANGIBLE SECUREMENT MEANS FOR INWARDLY DISPOSED SECUREMENT PANELS" and filed in the U.S. Patent and Trademark Office on Aug. 9, 1995 abandoned. The entirety of this application is hereby incorporated by reference.

FIELD OF THE INVENTION

This invention relates to disposable absorbent articles and particularly sanitary napkins having at least one laterally disposed panel secured to a longitudinal side thereof. More particularly, this invention relates to sanitary napkins having a substantially inwardly disposed securement panel that is frangibly secured in an outwardly position prior to use.

BACKGROUND OF THE INVENTION

The present invention relates to an absorbent article, such as a sanitary napkin, panty liner, adult incontinent garment and the like which are intended to be worn in the crotch portion of a pair of underpants. The basic form of such absorbent article is well known and typically includes a bodyside liquid-permeable cover, a garment-side liquid-impermeable baffle and an absorbent core positioned between the cover and the baffle. Numerous variations of the elements in addition to the basic cover, baffle and absorbent core arrangement are known. Each additional element is usually directed to improving a specific characteristic of the absorbent article. Such absorbent articles are now in a wide use as sanitary napkins, panty shields, panty liners and adult incontinence pads. While this invention is directed to all such products, for purposes of simplification, this invention will be described with reference to a sanitary napkin.

Present day commercial products have performed well, remaining in place and providing the user with ease of placement and removal. However, some of these products suffer from certain drawbacks. For example, the inner crotch surface of an undergarment, to which these products are typically adhered, is continually being distorted, twisted and stretched due to the dynamics of the wearer. As a result, the adhesive attachment can detach causing the undesirable consequence of the sanitary napkin moving out of place. Further, while the sanitary napkin frequently reattaches, due to the continuing adhesive nature of the pressure sensitive adhesive, reattachment often places the sanitary napkin in an undesirable position wherein the sanitary napkin does not function properly. In an extreme case, the attachment of the adhesive also results in the adhesive folding over on itself and then becoming unavailable for reattachment. In an effort to overcome the loss of protection due to the lack of close contact with the body of the wearer, and to ameliorate the above problem, disposable absorbent articles have been equipped with a pair of side panels, flaps or wings. As used herein "panels, flaps or wings" will hereinafter be collectively referred to as panel(s).

Generally prior to use, the panels are disposed to extend transversely from the longitudinal side edge of the absorbent core. Accordingly, the panels can extend laterally outward from the longitudinal side edges or can extend inwardly from the longitudinal side edges. Regardless of their pre-use orientation, the panels are intended to be folded around the edges of the wearer's undergarment.

The panels potentially offer some functional improvements and advantages over a sanitary napkin without such panels. First, the panels protect the edges of the wearer's undergarment from being soiled by exudates excreted from the body. Second, the panels help to stabilize the sanitary napkin from shifting out of place, especially when the panels are affixed to the underside of the panty.

Each panel can be either integral with the cover and/or the baffle or can be fashioned from separate pieces of material attached to the sanitary napkin. When the panels are separate pieces of material, they can be either attached to the sanitary napkin at the longitudinal side edge or inward thereof. Although the panels have greatly assisted in properly orienting the sanitary napkin in the crotch of the undergarment and in protecting the undergarment from side leakage, the panels have been problematic in their initial placement into the crotch area of the undergarment.

Each panel can be provided with an attachment means, for affixing the panel underneath the garment-facing side of the wearer's panty. Typically, the attachment means includes a garment adhesive which can be provided with a release liner to protect the adhesive from contaminants, such as, dirt and to keep the adhesive from sticking to the skin of the wearer and/or extraneous surfaces prior to use. When the wearer is ready to use the sanitary napkin, the release liner is peeled from the garment adhesive to expose the adhesive surface. The panels are then secured on the underside of the panties, either affixed to the garment-facing side of the wearer's panty or affixed to themselves.

When securing inwardly disposed panels, the work involved (removing the various protective layers, folding the panels and securing the panels to either the undergarment or themselves) can be quite laborious. It is highly probable that during this operation one or both of the panels may become inadvertently adhered to the undergarment-facing surface of the sanitary napkin. Typically, in the process of extricating the adhered panel, the panel and/or the baffle may tear, ruining the sanitary napkin. To prevent this from happening, the user must hold the sanitary napkin and hold the panels away from the adhesive surface(s) with one hand and peel the release liner with the other hand.

Alternatively, the panels can be constructed from a stiff material. The stiff material allows the panels to remain folded back when the wearer directs the panels outward. However, a stiff material can cause discomfort to the wearer by scratching and chaffing the inner regions of the wearer's thighs. Therefore, there is a need for a sanitary napkin having a pair of panels which can be easily manipulated and applied to the crotch of the undergarment.

SUMMARY OF THE INVENTION

Briefly, this invention relates to a disposable absorbent article having at least one panel. The panel, which is a separate piece of material, is secured to the garment-facing surface of the sanitary napkin. The panel, which one would understand to include a fixed portion and a free portion, has the free portion positioned inwardly relative to its longitudinal side edge. The sanitary napkin also includes a frangible securement means affixed to one surface of the panel to hold the free portion in an outward direction until the wearer is ready to affix the panel. This allows the wearer to easily position the sanitary napkin in the undergarment for use without incurring the difficulty described above for inwardly facing panels.

The general object of the present invention to provide an absorbent article, such as a sanitary napkin, with a pair of attachment panels. More specifically, an object of the invention is to provide an absorbent article with an inwardly disposed panel initially directed outwardly so that the panel will not interfere with the application of the sanitary napkin to the panty.

Another object of the invention is to frangibly secure an inwardly disposed panel outwardly prior to use.

These and other objects of the present invention will be more readily apparent when considered in reference to the following description and when taken in conjunction with the accompanying drawings.

BRIEF DESCRIPTION OF THE DRAWINGS

FIG. 1 is a top or body side view of a sanitary napkin having a pair of panels initially disposed in an outward position before the wearer would break the frangible bond.

FIG. 2 is a bottom or garment-facing view of the sanitary napkin shown in FIG. 1 illustrating the frangible bond broken and the two panels closed, as would be the typical arrangement for the panels in use.

FIG. 3 is a cross-sectional view taken along line 3—3 of FIG. 1.

FIG. 4 is a partial, enlarged cross-sectional view of the sanitary napkin with the panel in the released, i.e. in use, position illustrating the relationship of the frangible bond to the sanitary napkin and panel.

DETAILED DESCRIPTION OF THE PREFERRED EMBODIMENT

Referring to the Figures, in which like numerals indicate like parts throughout the several views, a disposable absorbent article 10 is depicted. For purposes of illustration only, the disposable absorbent article 10 is exemplified as a sanitary napkin. One skilled in the art will readily understand the adaptability of the invention to other personal care and health care articles, such as, for example, panty liners, adult incontinence garments and the like that use a securement panel to position the article relative to a wearer's undergarment. Typically, a sanitary napkin is worn by a female to absorb body fluids, such as menses, blood, urine and other body excrements discharged during a menstrual period. The term "disposable", as used herein, means that the absorbent article is discarded after a single use and is not intended to be laundered for subsequent reuse.

Referring to the Figures, a preferred embodiment of a sanitary napkin 10 is shown. The sanitary napkin 10 basically includes elongated absorbent pad 12 and a pair of panels 14 and 16. While it is not necessary for the sanitary napkin 10 to have two panels, two panels are preferred over one panel. Also while it is not necessary for the panels 14 and 16 to be mirror images of one another they preferably are, excepting, of course, their attachment means.

The form and construction of the absorbent pad 12 is generally conventional and it will be described only briefly. An absorbent 18 is enclosed between a liquid-permeable cover 20 and a liquid-impermeable baffle 22. The baffle 22 carries a central longitudinal strip of garment adhesive 24, covered, before use, by a conventional peel strip or release paper 26. Garment adhesive 24 thus extends in a longitudinal direction represented by longitudinal line "L".

Looking at the elements in greater detail, the cover 20 is fluid pervious and is adapted to reside on that side of the sanitary napkin 10 in contact with the body of the wearer. The cover 20 is provided for comfort and conformability and functions to direct body fluid to the adjacent absorbent 18. Preferably, the cover 20 is made of a material which allows the passage of fluid without wicking it appreciably in a horizontal plane parallel to the cover 20. The cover 20 should retain little or no fluid in its structure so that it provides a relatively dry surface next to the wearer's skin. The cover 20 can be constructed of any woven or nonwoven material which is easily penetrated by body fluid contacting its surface. Suitable materials include bonded carded webs of polyester, polypropylene, polyethylene, nylon, or other heat-bondable fibers, polyolefins, such as copolymers of polypropylene and polyethylene, liner low-density polyethylene, finely perforated film webs and net material also work well. Other suitable materials are composite materials of a polymer and a nonwoven fabric material. The composite sheets are generally formed by extrusion of a polymer onto a web of spunbond material to form an integral sheet. The liquid-permeable cover 20 can also contain a plurality of apertures (not shown) formed therein which are intended to increase the rate at which body fluids can penetrate down into the absorbent 18.

The cover 20 can have at least a portion of the bodyfacing surface treated with a surfactant to render the cover 20 more hydrophilic. This results in permitting the insulting liquid to more readily penetrate the cover 20. The surfactant also diminishes the likelihood that the insulting fluid, such as menstnial fluids, will flow off the cover 20 rather than being absorbed by the absorbent core 18. It is preferred that the surfactant be substantially evenly and completely distributed across at least the portion of the bodyfacing surface of the cover 20 that overlays the absorbent 18 of the sanitary napkin 10.

The absorbent 18 is generally composed of one or more materials that are hydrophilic, compressible, conformable and non-irritating to the wearer's skin. Acceptable materials are known in the art and include, for example, various natural or synthetic fibers, wood pulp fibers, regenerated cellulose or cotton fibers, or a blend of pulp and other fibers, meltblown polymer, such as polyethylene and polypropylene. The absorbent layers may also be comprised of other known materials used in absorbent articles such as cellulose sponge, hydrophilic synthetic sponge, such as polyurethane, and the like. The total absorbent capacity of the absorbent 18 should be compatible with the design exudate loading for the intended use of the sanitary napkin 10.

The absorbent 18 car contain superabsorbent materials which are effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids.

Superabsorbents can be incorporated into the absorbent 18 as separate layers or admixed with the cellulose fluff. Superabsorbents may be in the form of flakes, granules, films, particles, fibers or the like.

Although not shown in the drawings, the absorbent 18 may also include other features, such as a liquid-dispersing layer or a reinforcing layer made, for instance, of tissue or fabric.

The baffle 22 resides on the undergarment-facing surface of the absorbent pad 12 and may be constructed from any desired material that is liquid-impermeable. Preferably, the baffle 22 will permit the passage of air and moisture vapor out of the sanitary napkin 10 while blocking the passage of body fluids. A good material is a micro-embossed polymeric film, such as polyethylene or polypropylene, having a thickness of about 0.025 to 0.13 millimeters. Bicomponent films can also be used as well as woven and nonwoven fabrics which have been treated to render them liquid-impermeable.

Another suitable material is a closed cell polyolefin foam. A closed cell polyethylene foam having a thickness ranging from about 0.5 millimeters to about 10 millimeters works well.

Referring to FIGS. 2 and 3, the cover 20 and the baffle 22 extend beyond the absorbent 18 and are bonded together to form a peripheral seal 28. The cover 20 and baffle 22 can be bonded together using any means commonly known in the art for this purpose, such as by gluing, crimping, pressure and/or heat-sealing and ultrasonics. The peripheral seal 28 is illustrated as completely surrounding the absorbent core 18. This is the preferred embodiment for ease of construction. The peripheral seal 28 extends from a seal line 30, which closely borders the absorbent 18, to an outer peripheral edge 32. Along the longitudinal sides of the absorbent pad 12, the peripheral seal 28 extends from the longitudinal side edges 34 and 36 of the absorbent 18 to the respective longitudinal sides 38 and 40 of the sanitary napkin 10. The longitudinal sides 38 and 40 have upper and lower walls 42, 44 and 46, 48 respectively, formed by the respective extensions of the cover 20 and the baffle 22.

Each panel 14 and 16 is made of a separate piece of material. Suitable materials for the attachment panels 14 and 16 include polymeric foams, nonwovens, elastomers, or composites of these materials. As can be seen in FIG. 1, the panels 14 and 16 each consist of a generally rectangular sheet of material having a first end 60 and a second end 62 which, in assembly, has a fixed or attachment portion 50 and, extending from it, a free portion 52. The fixed portion 50 is bonded to the garment facing surface of the baffle 22, at the second end 62 of the panel and preferably, is affixed to the baffle 22 between the longitudinal side 34 and 36 of the absorbent 18 and the outer peripheral edge 32. More preferably, the fixed portion 50 is coterminous with the outer peripheral edge 32. By making each panel 14 and 16 from a separate piece of material and securing the panel 14 to the garment-facing surface of the baffle 22 there is no direct connection between the cover 20 and the panels 14 and 16. This effectively interrupts the path of liquid transport otherwise possible if the panels 14 and 16 were integrally formed from an extension of the cover 20, the baffle 22 or both.

The overall shape and size of the panels 14 and 16 can be readily selected depending upon the shape, size, thickness and intended use of the product. Accordingly, the panels 14 and 16 can have a length which would extend across the width of the sanitary napkin 10 Desirably, two panels 14 and 16 are employed so that each panel could extend a distance less than the width of the sanitary napkin 10 Preferably, the panels 14 and 16 are sized in accordance with the dimensions given in Table 1 below.

TABLE 1

| Dimensions (inches) | Nominal | Range | Preferred Range |
| --- | --- | --- | --- |
| Pad Length | 9.0 | 7.0–13.0 | 8.0–11.0 |
| Pad Width | 3.5 | 2.0–4.5 | 2.5–4.0 |
| Panel Length | 2.0 | 1.0–5.0 | 1.5–3.0 |
| Panel Width | 2.25 | 1.5–2.75 | 1.75–2.5 |

FIGS. 1—3 also show fastening means 54 and 56 secured to the panels 14 and 16 respectively. The fastening means 54 and 56 are adapted to secure the sanitary napkin 10 to the crotch region of a wearer's undergarment. Each fastener 54 and 56 can be a mechanical fastener such as a hook-and-loop arrangement (for example, "VELCRO"), snaps, buttons, and the like. Other fasteners suitable for securing the panels 14 and 16 under the crotch region of the undergarment includes the use of an adhesive on one or both of the panels 14 and 16.

Substantially the entire length of each panel 14 and 16 is held in a laterally outward position (substantially in a transverse or lateral direction represented by transverse line "T") prior to use by a frangible fastener 58 as shown in FIGS. 1 and 3. The terms "inward" and "outward" are descriptive of the free portion 52 orientation as directed substantially toward absorbent 18 or directed substantially away from absorbent 18 substantially in a transverse or lateral direction represented by transverse line "T", respectively. To maintain the integrity of each panel 14 and 16 and still retain each panel 14 and 16 in an outward position prior to use, the frangible fastener 58 should have a bond strength of less than about 500 grams, preferably the frangible bond 58 has a bond strength of less than about 200 grams, and more preferably it has a bond strength less than about 50 grams. The bond strength of the frangible fastener 58 is determined using an Instron Tester, available from the Instron Corporation, P.O. Box 39384, Minneapolis, Minn. 55439-0384. To determine the force necessary to break the bond of each frangible fastener 58, the free end 52 of each panel 14 and 16 is placed in the opposing jaws of the instrument. The instrument is engaged and peak load when the bond releases is recorded.

Each frangible fastener 58 can be any attachment means that will readily release when a force, as specified above, is applied to the frangible fastener 58. Suitable frangible means include low tack adhesives, such as a hot melt adhesive, that will be substantially non-tacky after the bond is broken, pin punching and ultrasonic bonds. Mechanical fasteners, such as hook-and-loop, buttons, snaps, and the like may be used but are not preferred because after the bond is broken the exposed surface of the mechanical fastener may cause irritation to the wearer during use. The size of each frangible fastener 58 needed to orient the free portion 52 of each panel 14 and 16 outwardly can vary depending on a number of factors. These include, but are not limited to, the size and configuration of each panel 14 and 16, the type of frangible fastener 58 selected and the distance between the fixed portion 50 of each panel 14 and 16 and the peripheral edge 32 of the sanitary napkin 10. Desirably, the frangible fastener 58 is an ultrasonic bond having a surface area ranging from about 0.2 square millimeters (mm$^2$) to about 13 mm$^2$. Preferably the bond has a surface area ranging from about 0.5 square mm to about 10 mm$^2$, and more preferably, the bond has a surface area ranging from about 2 mm$^2$ to about 10 mm$^2$.

Referring to FIG. 4, only panel 14 will be described for purposes of clarity. The frangible fastener 58 can be positioned anywhere on the sanitary napkin 10 that will affix the free portion 52 of the panel 14 in an initially outward direction, i.e., prior to the wearer fracturing the bond(s). The frangible fastener 58 is fastened to at least one surface of the panel 14 and desirably, it is fastened to the garment facing surface of the panel 14. The frangible fastener 58 can be positioned at the outer peripheral edge 32 or inward from the outer peripheral edge 32 a predetermined distance "Z" to prevent the frangible fastener 58 from irritating the wearer after the bond has been broken. The distance "Z" can be from about 0.5 millimeters to about 6.0 millimeters. Preferably, the distance "Z" is from about 0.5 millimeters to about 3.0 millimeters. More preferably, the frangible fastener 58 is positioned on the panel 14 at a location that is between the outer peripheral edge 32 and the longitudinal side edge 34 of the absorbent 18.

The sanitary napkin 10 of the present invention is utilized by removing the release liner 26 and placing the sanitary napkin 10 in a crotch region of an undergarment (not shown). The baffle 22 is placed in contact with the inner surface of the center crotch portion of the panty. The central garment adhesive 24 maintains the absorbent pad 12 in position. The bond formed by the frangible fastener 58 is broken so that the free portion 52 of the two panels 14 and 16 can be folded around the edges of the undergarment. The panels 14 and 16 are then secured underneath the crotch portion of the undergarment.

While there has been shown and described certain preferred embodiments in accordance with the invention, it will be appreciated that many variations and modifications may be made therein without departing from the essential spirit of this invention.

We claim:

1. A sanitary napkin comprising:
    a) a bodyside cover;
    b) an undergarment-facing baffle;
    c) an absorbent having at least one longitudinal side edge, said cover and said baffle extending beyond said at least one side edge to enclose said absorbent and define an outer peripheral edge;
    d) a panel having first and second ends, said second end of said panel being secured to said baffle to define a fixed portion of said panel, with the remainder of said panel defining, during use, an unfolded inwardly oriented free portion; and
    e) frangible securement means for frangibly securing said free portion to said fixed portion of each of said panels to fold said free portion in an outward position in a transverse direction, prior to use;
    said free portion of said panel being inwardly oriented toward said absorbent after said securement means is broken.

2. The sanitary napkin of claim 1 wherein said securement means has a bond strength of less than about 500 grams.

3. The sanitary napkin of claim 1 wherein said frangible securement means has a bond strength less than about 50 grams.

4. The sanitary napkin of claim 1 wherein said frangible securement means is a hot melt adhesive.

5. The sanitary napkin of claim 1 wherein the second end of said panel is co-terminous with said outer peripheral edge.

6. The sanitary napkin in claim 1 wherein the second end of said panel is inboard of said outer peripheral edge.

7. The sanitary napkin of claim 1 wherein said securement means has a frangible bond strength of less than about 200 grams.

8. The sanitary napkin of claim 1 wherein said frangible securement means is an ultrasonic bond having a surface area ranging from about 0.2 square millimeters to about 13 square millimeters.

9. The sanitary napkin of claim 1 wherein said frangible securement means is selected from adhesives, ultrasonic bonds, mechanical fasteners and combinations thereof.

10. The sanitary napkin of claim 9 wherein said frangible securement means is an ultrasonic bond having a surface area ranging from about 0.2 square millimeters to about 13 square millimeters.

11. A sanitary napkin having a transverse direction and a longitudinal direction, said sanitary napkin comprising:
    a) a body-side cover;
    b) an undergarment-facing baffle;
    c) an absorbent having at least one longitudinal side edge, said cover and said baffle extending beyond said at least one side edge to enclose said absorbent and define an outer peripheral edge;
    d) a pair of panels, each of said panels having first and second ends, said second end of each of said panels being secured to said baffle to define a fixed portion of each of said panels with the remainder of each of said panels defining with said fixed portion, during use, an unfolded inwardly oriented free portion; and
    e) frangible securement means securing said free portion of each of said panels to said fixed portion of each of said panels to said to fold said free portion in a position extending substantially outwardly in the transverse direction prior to use;
    whereby said free portion of each said panel is restored to its position extending inwardly after the frangible bond is broken.

12. The sanitary napkin of claim 11 wherein said frangible securement means comprises a hot melt adhesive.

13. The sanitary napkin of claim 11 wherein said securement means comprises a mechanical fastener.

14. The sanitary napkin of claim 11 wherein said securement means is affixed to said fixed portion of said panel adjacent said outer peripheral edge.

15. The sanitary napkin of claim 11 wherein said securement means is affixed to said fixed portion of said panel inward from said outer peripheral edge.

16. The sanitary napkin of claim 11 wherein said securement means is positioned inward from the outer peripheral edge a distance from about 0.5 millimeters to about 3.0 millimeters.

17. A sanitary napkin comprising:
    a) a bodyside cover;
    b) an undergarment-facing baffle;
    c) an absorbent having at least one longitudinal side edge, said cover and said baffle extending beyond said at least one longitudinal side edge to enclose said absorbent and define an outer peripheral edge;
    d) a pair of panels, each of said panels having first and second ends, said second end of each of said panels being secured to said baffle to define a fixed portion of each of said panels with the remainder of each of said panels defining, during use, an unfolded inwardly oriented free portion; and
    e) a frangible ultrasonic bond securing said free portion of each said panel to said fixed portion such that substantially the entire length of said free portion of each said panel extends in an outward position substantially in a transverse direction prior to use, breaking of said ultrasonic bonds enabling said free portion of each said panel to extend inwardly.

18. The sanitary napkin of claim 17 wherein the ultrasonic bond for each panel has a surface area ranging from about 0.2 square millimeters to about 13 square millimeters.

19. The sanitary napkin of claim 17, the first end of each of said panels having a fastener, said fasteners being secured to each other when the sanitary napkin is deployed for use.

* * * * *

UNITED STATES PATENT AND TRADEMARK OFFICE
CERTIFICATE OF CORRECTION

PATENT NO. : 6,013,062
DATED : January 11, 2000
INVENTOR(S) : Rebecca Lyn Dilnik It is certified that error appears in the above-identified patent and that said Letters Patent is hereby corrected as shown below:

Column 1,
Line 32, delete "a".

Column 4,
Line 43, delete "car" and insert -- can -- in place thereof.

Column 5,
Line 30, delete "," after "22".

Column 6,
Line 16, delete "bond" and insert -- fastener -- in place thereof.

Claim 6,
Line 1, delete "in" and insert -- of -- in place thereof.

Claim 11,
Line 17, after "panels to" delete "said to", delete "porlion" and insert -- portion -- in place thereof.

Signed and Sealed this

Thirtieth Day of October, 2001

Attest:

NICHOLAS P. GODICI
*Acting Director of the United States Patent and Trademark Office*

*Attesting Officer*